United States Patent [19]

Seare

[11] Patent Number: 5,356,429
[45] Date of Patent: Oct. 18, 1994

[54] BODY POCKET MAINTENANCE PROSTHESIS

[76] Inventor: William J. Seare, 3396 Chula Vista Cir., Salt Lake City, Utah 84121

[21] Appl. No.: 960,004

[22] Filed: Oct. 13, 1992

Related U.S. Application Data

[63] Continuation of Ser. No. 701,021, May 16, 1991, abandoned.

[51] Int. Cl.$^5$ ............................. A61F 2/12; A61F 2/02
[52] U.S. Cl. ............................................ 623/8; 623/11
[58] Field of Search .................... 623/8, 7, 11, 13, 14, 623/66

[56] References Cited

U.S. PATENT DOCUMENTS

| | | |
|---|---|---|
| 3,577,837 | 5/1971 | Bader, Jr. . |
| 4,298,998 | 11/1981 | Nacify ............................. 623/8 |
| 4,585,458 | 4/1986 | Kurland . |
| 4,597,763 | 7/1986 | Schweikhart .................... 623/8 |
| 4,676,795 | 6/1987 | Grundei ............................ 623/8 |
| 4,685,447 | 8/1987 | Iversen et al. . |
| 4,773,909 | 9/1988 | Chaglassian ..................... 623/8 |
| 4,790,848 | 12/1988 | Cronin ............................ 623/8 |
| 4,994,084 | 2/1991 | Brennan . |

Primary Examiner—David Isabella
Attorney, Agent, or Firm—Thorpe North & Western

[57] ABSTRACT

A body pocket maintenance prosthesis for implanting in a submuscular/subglandular implant pocket formed in a human female's chest in conjunction with a mammary implant. The maintenance prosthesis includes at least one sheet of elastomeric material formed generally in a partly-annular configuration to at least partially surround the mammary implant in the implant pocket, with the sheet of material having a textured side to allow growth thereon of human tissue of the pocket wall against which the textured side is placed, and a smooth, non-textured side to inhibit the growth thereon of human tissue. The mammary implant is thus allowed to move or flow in the body pocket to locations between the smooth side of the sheet of material and the adjacent body pocket wall.

10 Claims, 1 Drawing Sheet

BODY POCKET MAINTENANCE PROSTHESIS

This application is a continuation of application Ser. No. 07/701,021 filed May 16, 1991, now abandoned.

BACKGROUND OF THE INVENTION

The present invention relates to a prosthesis for implantation in a body and more particularly to a prosthesis for maintaining the existence of a pocket or surface, either natural or surgically made, in the body and preventing the walls of the pocket or surface from adhering together or from adhering to tissue or organs.

Prostheses for implantation in the human body are well known, having been used for breast augmentation, nose, ear and other body part reconstruction, lymphedema shunts, percutaneous skin access devices, insulin implants, paraplegic implantable cushions, tendon repair prosthesis, etc. Of course, perhaps the most well-known implantable prosthesis, and the most commonly used, is the prosthesis used for either breast reconstruction or breast augmentation. The procedure for using these prostheses typically involves forming a pocket, referred to hereafter as a body pocket, or cavity in a patient's breast and extending submuscularly/subglandularly/subcutaneously upwardly to overlay the superior/lateral part of the chest. This may involve simply the dissection of tissue in the breast area to form the pocket or the dissection of tissue as well as removal of diseased or unwanted tissue. In either case, a fairly large pocket is formed over much of the chest area.

After formation of the body pocket, the selected implantable primary prosthesis (now typically constructed of a silicone envelope in which is contained some type of elastomer gel, liquid saline, or other fluid) is placed at the desired site in the body pocket or cavity which best provides the desired augmentation (or reconstruction) and appearance. Immediately after the implantation, the implanted envelope (as the primary prosthesis) is allowed to "flow" or move within the dissected pocket superiorly and laterally to give the breast an anatomically natural look and feel. However, after time, usually a matter of weeks, facing walls of the body pocket begin to re-adhere and a natural tissue capsule forms around the implant to prevent it from flowing or moving in the pocket. This natural tissue capsule may also contract to tighten around the implanted prosthesis causing it to be unnaturally firm, possibly distorted in form, and sometimes painful.

Of course, with either reconstructive or augmentation surgery of a breast, it is desired that the resulting feature remain as natural in both appearance and feel as possible for as long as possible. With the procedures currently used, achieving this objective consistently is very difficult.

SUMMARY OF THE INVENTION

It is an object of the invention to provide a method and structure for maintaining a body pocket in a desired configuration and of preventing re-adherence together of at least some of the body pocket walls.

It is also an object of the invention to provide a method and structure by which a more natural look and feel may be maintained in a body implant prosthesis.

It is an additional object of the invention to provide such a method and structure where the natural movement and flow of an implantable primary prosthesis is preserved.

It is another object of the invention to provide a simple, easy to implant auxiliary prosthesis for use with breast augmentation and breast reconstruction prostheses.

It is still a further object of the invention to provide such a method and structure which allows easy replacement of or inclusion with an existing encapsulated prosthesis, of a prosthesis made in accordance with the present invention.

It is still another object of the invention to provide tissue ingrowth into a porous surface of an implant and reduce or prevent fibrous capsular contracture at that point which is replaced on the adjoining surface by a smooth, flexible, non-contracting surface.

The above and other objects of the invention are realized in a specific illustrative embodiment of a body pocket maintenance prosthesis comprised of a sheet of elastomeric material for disposition in a body pocket formed by surgical dissection. The sheet of elastomeric material is formed in a partly-annular configuration to at least partially surround another implantable prosthesis to prevent re-adherence of the body pocket walls which are positioned adjacent the sheet of material on each side thereof. One side of the sheet is formed to be smooth and non-textured so that adherence to the contiguous body pocket wall will be inhibited, whereas the other side is textured to allow growth thereon (or therein) of human tissue of the corresponding contiguous body pocket wall. In this manner, one side of the sheet of material adheres to a body pocket wall so that the sheet is held in place, but the other side does not so adhere so that the other implantable prosthesis may move into the space between the smooth side of the sheet and the contiguous body pocket wall. This allows a freer flow movement of the other implantable prosthesis and thus a more natural look and feel for such prosthesis. It also allows separate control of the amount and shape of the surface area of the body pocket which is not related to the amount or shape of the surface area of the implanted primary prosthesis.

BRIEF DESCRIPTION OF THE DRAWINGS

The above and other objects, features and advantages of the invention become apparent from a consideration of the following detailed description presented in connection with the accompanying drawings in which.

DETAILED DESCRIPTION

Figure 1:
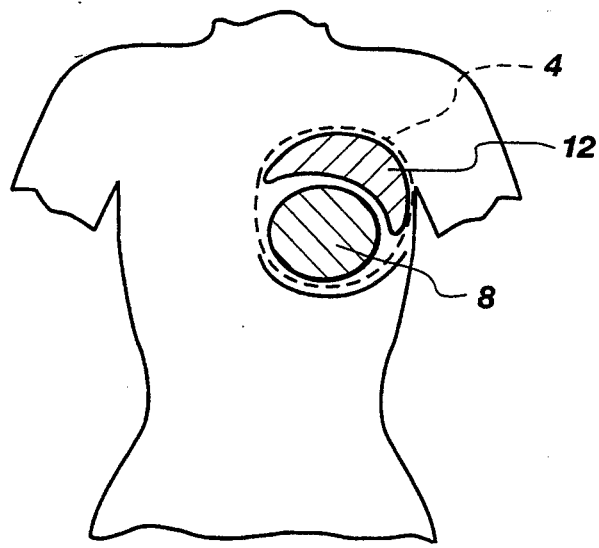
FIG. 1 is a front, graphic view of a body pocket maintenance prosthesis made in accordance with the principles of the present invention.

Referring to FIG. 1, there is shown a front, graphic view of a portion of a female's torso including the chest area, showing one illustrative way in which the body pocket maintenance prosthesis of the present invention may be used. In female breast reconstruction or augmentation, it is typical to first form a pocket 4 in a patient's chest to extend submuscularly/subglandularly/subcutaneously to overlay the superior/lateral part of the chest as shown. Such a pocket may be formed by dissecting the tissue in the breast area and, in some instances, removing a part of the breast tissue to thereby create a fairly flat void or pocket having facing pocket walls.

Into such a pocket 4 is implanted a primary prosthesis 8 (such as a mammary prosthesis), typically constructed with a silicone envelope in which is contained some type of elastomer gel, liquid saline, or other liquid, to form a dome-like or somewhat flattened spherical body. The prosthesis 8 occupies only a portion of the body pocket 4 so that the prosthesis is allowed to move, flatten, and generally imitate in feel and appearance a female breast. In effect, the prosthesis 8 is allowed to move or "flow" to various locations in the pocket 4 to provide the more desired natural look and feel. With the insertion of prosthesis 8, the surface area, both amount and shape, can be controlled.

As indicated earlier, over time the facing walls of the body pocket 4 begin to re-adhere or grow together where they were allowed to touch, resulting in the formation of a natural tissue capsule around the prosthesis 8. This natural tissue capsule prevents the prosthesis 8 from flowing or moving in the pocket 4 and presents a hardened and in many cases distorted feel and appearance for the prosthesis.

The present invention of a body pocket maintenance prosthesis, shown at 12 in FIG. 1, serves to prevent the body pocket 4, and in particular the facing walls of the body pocket, from growing together, to thus prevent the formation of a natural tissue capsule and the resultant hardening of the pocket surrounding the prosthesis 8. The maintenance prosthesis 12 is positioned in the pocket 4 just above the mammary prosthesis 8 and is formed to have a generally part-annular or crescent configuration so as to partially surround the prosthesis 8.

The body pocket maintenance prosthesis 12 may be formed of a single sheet of elastomeric material such as silicone, collagen, polyurethane, expanded polytetrafluoroethylene microporous film, or other flexible elastomeric material, one side of which is textured such as by making the side porous to a certain depth. One method of producing a textured, porous side for the prosthesis 12 is disclosed in U.S. Pat. No. 4,889,744. Of course other methods could be used to provide a textured surface on one side of the sheet including mechanical means such as simply piercing or puncturing the selected side's surface, as well as chemical etching methods, solid leaching methods or gluing an open-celled porous material such as polyurethane foam, silicone foam, or flexible fabric meshes of various sorts to one side.

The other side of the single sheet is formed to be smooth and non-textured to thereby provide a sheet of elastomer material one side of which (the smooth side) will not adhere or allow growth thereonto of tissue against which it is positioned, and the other side of which (the textured side) will allow growth thereonto of tissue against which it is positioned. Thus, one side of the body pocket maintenance prosthesis sheet adheres to one of the body pocket facing walls so that the sheet is held in place, while the other side does not so adhere and allows the flow or movement between that side and the adjacent body pocket wall of the mammary prosthesis 8. As a consequence, the mammary prosthesis 8 retains a more anatomically natural look and feel such as, for example, when being pressed, when the person is lying on her back or chest, and during palpation.

The thickness of a single sheet maintenance prosthesis might illustratively be twenty to forty thousandths of an inch with the length and width dimensions being selected to partially surround the mammary prosthesis and substantially fill that portion of the body pocket not occupied by the mammary prosthesis, as desired.

Figure 2:
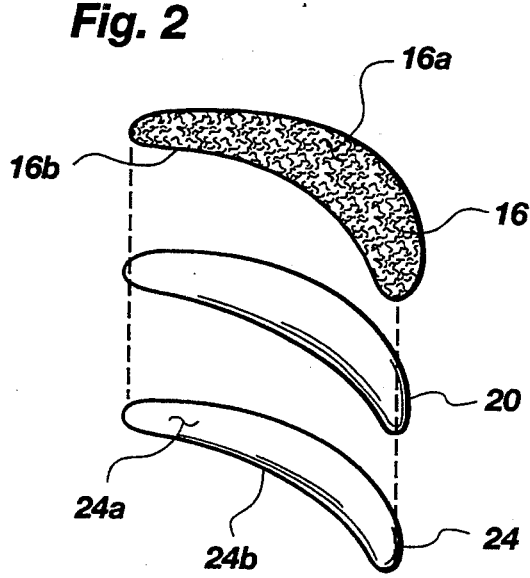
FIG. 2 is a perspective, exploded view of one embodiment of the body pocket maintenance prosthesis of the present invention.

Another embodiment of the body pocket maintenance prosthesis of the present invention includes use of two sheets of elastomeric material, one placed on top of the other, with the two outside oppositely facing sides of the sheets being textured, and the two inside facing sides of the sheets being smooth and non-textured to readily slide with respect to one another. This embodiment is illustrated in FIG. 2 and would include sheet 16 and sheet 24, with sheet 20 not being used. Top side 16a of the sheet 16 is textured, as is bottom side 24b of sheet 24, with the bottom side 16b of sheet 16 and the top side 24a of sheet 24 being smooth and non-textured.

With the two sheet embodiment of the invention, the two textured sides or surfaces of the respective sheets would adhere to corresponding facing walls of the body pocket so as to become fixed thereto, and the smooth facing sides of the two sheets would thus be free to readily slide over one another and to separate and allow movement therebetween of the mammary prosthesis 8 of FIG. 1. Again, this would allow for more natural movement of the mammary prosthesis and would prevent the growing together of the previously facing walls of the body pocket into which the mammary prosthesis was implanted.

A three sheet embodiment of the present invention is also shown in FIG. 2 and includes, along with the previously described sheets 16 and 24, a third sheet of elastomeric material 20 disposed between the sheets 16 and 24. The top and bottom sides of the sheet 20 are both smooth and non-textured to readily allow the respective adjacent sheets 16 or 24 to slide thereover. A mammary prosthesis would thus be allowed to move in between either sheet 16 and 20 or between sheets 20 and 24 to again provide the desired natural flow and look of the mammary prosthesis. Of course, any number of sheets of material could be used depending on the thickness desired of the maintenance prosthesis.

Figure 3:
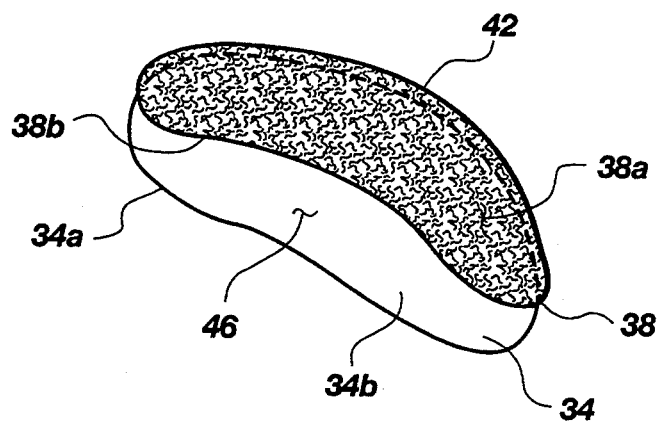
FIG. 3 is a perspective view of another embodiment of the body pocket maintenance prosthesis of the present invention.

FIG. 3 shows still another embodiment of a body pocket maintenance prosthesis which includes two sheets of elastomeric material 34 and 38, joined together by gluing, sewing, etc. at one edge 42 as indicated. The opposite edges of the sheets 34 and 38 are free to flare apart to reveal a pocket 46 as shown. The exterior sides 34a and 38a of the sheets are textured, and the two facing sides 34b and 38b are non-textured and smooth to readily allow for movement of, for example, a primary prosthesis such as prosthesis 8 of FIG. 1, into and out of the pocket 46. This, of course, would provide for a more natural exterior look and feel to the primary prosthesis, as desired. It would also provide a greater amount of surface area of the pocket or cavity to be lined with the prosthetic material and thereby limit the normal fibrous capsule, which is known to become thickened and contract.

Although the body pocket maintenance prosthesis has been described specifically as it might be used with a mammary implant, it should be understood that the maintenance prosthesis could be used in any circumstance or situation where it was desired to prevent (or control) the walls of a body pocket from adhering or growing together. Examples of such situations include implantation onto the peritoneal surface of the abdominal cavity to prevent fibrous tissue adhesions or to prevent re-adherence of adhesions after they are excised.

Another example involves implantation of the prosthesis of the present invention into a pocket where tissue expansion is being undertaken-this allows for a broader and more extensive surface area, with more specific directionality, to be expanded. In this latter case, if the textured or porous surface were formed from a material which is known to prevent or reduce capsular contracture in the tissue which is adjacent or has grown into the porous or textured surface, a more rapid and compliant tissue expansion can proceed due to the greater surface area of the pocket and the more compliant (less capsular contracture) tissue beneath the porous surface. For example: FIG. 2, sheet 20 could be a tissue expansion prosthesis fitted between sheets 16 and 24, and the above result could be achieved.

Still another example of use of the present invention would be the placement of a sheet of elastomeric material in a fractured eye socket, with the smooth side disposed against the eyeball and fatty contents and the textured side disposed against and fixated to the lower bony infraorbital plate so as to prevent herniation through an orbital plate fracture.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A body implant comprising a body pocket maintenance prosthesis for implantation into a body pocket a mammal, including, a first sheet of elastomeric material having first and second sides for placement within the body pocket to prevent the body pocket walls from growing together, the first side of said sheet being smooth and non-textured to inhibit adhesion thereto of human tissue, and the second side of said sheet being textured to allow growth thereinto of human tissue so that the textured second side of the sheet adheres to a contiguous body pocket wall while the smooth first side of the sheet does not so adhere to a corresponding contiguous body pocket wall;

a primary prosthesis for implantation into the body pocket and adapted for movement therein between the body pocket walls and adjacent the smooth first side of the sheet, whereby movement of the primary prosthesis within the body pocket is uninhibited due to the prevention of the growing together of the body pocket walls; and a second sheet of elastomeric material having first and second sides for placement inside the first sheet in the body pocket, the first side of said second sheet being smooth and non-porous and positioned contiguous to the smooth first side of said first sheet to freely slide relatively thereto, and the second side of said second sheet being porous to allow growth of human tissue.

2. A body pocket maintenance prosthesis as in claim 1 further comprising one or more additional sheets of elastomeric material disposed between the first and second sheets of material.

3. A body pocket maintenance prosthesis as in claim 1 wherein said first and second sheets of material are joined together at contiguous edges to allow opposite edges of the sheets to spread apart to define a pocket therebetween.

4. A prosthesis for implanting in a submuscular, subglandular or subcutaneous implant pocket formed in a human female's chest in conjunction with a primary implant adapted for implantation in the implant pocket, said prosthesis comprising at least a first sheet of elastomeric material formed in a partly annular, flat configuration said sheet of material having a porous side to allow growth thereon of human tissue of the pocket against which the porous side is placed, and a smooth, non-porous side to inhibit the growth thereon of human tissue, whereby the first sheet partially surrounds the primary implant in the implant pocket; and a second sheet all of elastomeric material having first and second sides disposed in a stack with said first sheet, wherein the first side of the second sheet is contiguous with the smooth side of the first sheet, with the second side of the second sheet furthest from said first sheet being porous.

5. A prosthesis for implanting in a submuscular, subglandular or subcutaneous implant pocket formed in a human female's chest in conjunction with a primary implant adapted for implantation in the implant pocket, said prosthesis comprising at least a first sheet of elastomeric material formed in a partly annular, flat configuration, said sheet of material having a porous side to allow growth thereon of human tissue of the pocket against which the porous side is placed, and a smooth, non-porous side to inhibit the growth thereon of human tissue, whereby the first sheet partially surrounds the primary implant in the implant pocket; and a second sheet of elastomeric material formed in substantially the same configuration as the first sheet and joined at one edge to one edge of the first sheet to allow opposite edges of the sheets to spread apart to define a pocket into which and out of which the primary implant may move.

6. A method of maintaining separation of first and second facing walls of an implant pocket of a person comprising the steps of dissecting submuscular, subglandular or Subcutaneous tissue of the person to form the pocket, implanting at a selected location between selected portions of the facing walls of the pocket at least one first sheet of elastomeric material which includes one textured side, for allowing the growth thereon of tissue of the first facing wall of the pocket, and a smooth, non-textured side, for inhibiting the growth thereon of tissue of the second facing wall, to thereby maintain separation and prevent the adherence of the selected portions of the facing walls the first sheet of elastomeric material having a partially annular configuration to circumscribe a portion of an area in the pocket in which a primary implant is to be placed;

placing a primary implant into the pocket adjacent the smooth side of the first sheet; and implanting one or more additional sheets of elastomeric material stacked with the first sheet on the smooth, non-textured side thereof, and generally coterminous therewith, wherein an outside exposed side of the sheet farthest from the first sheet is textured to allow growth thereon of tissue of said second facing wall.

7. The method of claim 6 wherein said implanting step comprises implanting said sheets of elastomeric material made of a polyurethane material.

8. The method of claim 7 wherein said implanting step comprises implanting said sheets of elastomeric material made of material selected form the group consisting of silicone, polyurethane and expanded polytetrafluorethylene microporous film.

9. The method of claim 6 wherein said implanting step comprises implanting two sheets of elastomeric material joined at one side edge, with edges opposite said one edge being free to spread apart to define a pocket.

10. The prosthesis of claim 4 further comprising one or more additional sheets of elastomeric material disposed in a stack between the first and second sheets.

* * * * *